(12) United States Patent
Eidenschink (10) Patent No.: US 7,326,242 B2
(45) Date of Patent: Feb. 5, 2008

(54) ASYMMETRIC BIFURCATED CROWN (75) Inventor: Tracee Eidenschink, Wayzata, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 690 days.

(21) Appl. No.: 10/288,621

(22) Filed: Nov. 5, 2002

(65) Prior Publication Data

US 2004/0088007 A1 May 6, 2004

(51) Int. Cl.
A61F 2/82 (2006.01)
(52) U.S. Cl. ..................... 623/1.15; 623/1.35
(58) Field of Classification Search ............... 623/1.15, 623/1.35, 1.16, 1.17
See application file for complete search history.

(56) References Cited

U.S. PATENT DOCUMENTS

| 4,994,071 | A | 2/1991 | MacGregor | 606/194 |
|---|---|---|---|---|
| 5,282,860 | A | 2/1994 | Matsuno et al. | 623/12 |
| 5,540,712 | A * | 7/1996 | Kleshinski et al. | 623/1.19 |
| 5,800,508 | A | 9/1998 | Goicoechea et al. | 623/1 |
| 5,800,520 | A | 9/1998 | Fogarty et al. | 623/1 |
| 5,893,887 | A | 4/1999 | Jayaraman | 623/1 |
| 5,906,640 | A | 5/1999 | Penn et al. | 623/1 |
| 6,017,363 | A | 1/2000 | Hojeibane | 623/1 |
| 6,033,435 | A | 3/2000 | Penn et al. | 623/1 |
| 6,258,116 | B1 | 7/2001 | Hojeibane | 623/1.16 |
| 6,270,524 | B1 * | 8/2001 | Kim | 623/1.15 |
| 6,325,826 | B1 | 12/2001 | Vardi et al. | 623/1.35 |
| 6,749,628 | B1 | 6/2004 | Callol et al. | 623/1.15 |
| 2001/0014794 | A1 | 8/2001 | Moll et al. | 604/289 |
| 2001/0016768 | A1 | 8/2001 | Wilson et al. | 623/1.11 |
| 2001/0037137 | A1 | 11/2001 | Vardi et al. | 623/1.11 |
| 2002/0099436 | A1 | 7/2002 | Thornton et al. | 623/1.12 |
| 2002/0120325 | A1 | 8/2002 | Richter et al. | 623/1.11 |
| 2002/0193873 | A1 * | 12/2002 | Brucker et al. | 623/1.35 |

FOREIGN PATENT DOCUMENTS

EP   0 904 745 A3   3/1999

* cited by examiner

Primary Examiner—Michael Thaler
(74) Attorney, Agent, or Firm—Vidas, Arrett & Steinkraus, P.A.

(57) ABSTRACT

An expandable stent for percutaneous procedures comprises a tubular structure disposed about a longitudinal axis and a plurality of fingers. The plurality of fingers, upon expansion of the stent, extends from the tubular structure about a second longitudinal axis which is angularly offset from the first longitudinal axis. At least one of the plurality of fingers has a length that is greater than that of the other fingers.

9 Claims, 7 Drawing Sheets

ASYMMETRIC BIFURCATED CROWN

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable.

Within the vasculature it is not uncommon for stenoses to form at a vessel bifurcation. A bifurcation is an area of the vasculature or other portion of the body where a first (or parent) vessel is bifurcated into two or more tubular component vessels. Where a stenotic lesion or lesions form at such a bifurcation, the lesion(s) can affect only one of the vessels (i.e., either of the tubular component vessels or the parent vessel) two of the vessels, or all three vessels.

Many of the bifurcated stents that have been disclosed are deployed by two balloons. A first balloon expands the main section of the stent and a second balloon expands the branch.

In spite of the many bifurcated stents that have been disclosed, there remains a need for innovative bifurcated stents which may be deployed using a single balloon for the main section and an alternate mechanism for the side branch. There also remains a need for bifurcated stents with innovative designs in the region of the bifurcation to provide adequate coverage of the carina.

All US patents and applications and all other published documents mentioned anywhere in this application are incorporated herein by reference in their entirety. Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the invention is directed to an expandable stent having a tubular structure which is disposed about a first longitudinal axis and a plurality of fingers which, upon expansion of the stent, extend from the tubular structure about a second longitudinal axis. The second longitudinal axis is angularly offset from the first longitudinal axis. At least one of the plurality of fingers has a length that is greater than that of the other fingers. In the unexpanded state the fingers may lie substantially on the surface of the stent.

Desirably, the fingers are disposed about an opening of the stent. The fingers and the opening define a crown.

Another embodiment of the invention is directed to a stent with a crown having fingers in which one portion of the crown has fingers that have a shorter average length than the average length of fingers on another portion of the crown.

Another embodiment of the invention is directed to a stent with a crown having fingers in which the proximal portion of the crown has fingers with a longer average length than the average length of fingers on the distal portion of the crown.

Another embodiment of the invention is directed to a stent with a crown having fingers in which the proximal portion of the crown has fingers with a shorter average length than the average length of fingers on the proximal portion of the crown.

Another embodiment of the invention is directed to a stent in an unexpanded condition with a crown. The fingers on a more distal portion of the crown extend proximally in such a way that a portion of at least one finger on the distal portion is proximal to a portion of at least one finger on the proximal portion of the crown which extend distally such that the fingers overlap one another. Another embodiment is directed to fingers that are interlaced with one another.

Another embodiment of the invention is directed to a stent with a crown having fingers with a length between 10.0 and 0.5 mm; desirably between 7.0 and 1.0 mm; and more desirably between 5.5 and 1.5 mm.

Another embodiment of the invention is directed to a stent with a crown having fingers in which the fingers have varying lengths.

Another embodiment is directed to a stent with a crown that begins opening into the secondary lumen before the main body of the stent is fully deployed.

A further embodiment of the invention is directed to a bifurcated stent comprising a first tubular component and a second tubular component. The first tubular component has a longitudinal axis, and the second tubular component has a longitudinal axis angularly offset relative to the first longitudinal axis. The second tubular component extends from the first tubular component. The second tubular component has a plurality of fingers with at least one of the plurality of fingers having a length that is greater than that of the other fingers.

Another embodiment is directed to a bifurcated stent having a tubular structure with a first longitudinal axis and fingers extending therefrom. The fingers are positioned about a second longitudinal axis wherein at least one finger is longer than an adjacent finger. Desirably, the fingers are disposed about an opening.

Another embodiment is directed to a catheter for delivery of a stent. The catheter comprises an apparatus for expanding a crown of the stent. The apparatus has a pushing device with a proximal end region and a distal end region. The proximal end region corresponds to a proximal end of a catheter, and the distal end region is constructed and arranged to be positioned adjacent to the stent to expand the crown members when the pushing device is advanced.

The pushing device may be a rod or hypotube.

In another embodiment, the catheter comprises a balloon, and the stent is disposed about a portion of the balloon. At least a portion of the distal end region of the pushing device is fixedly attached to the balloon at a region of attachment with the distal end of the pushing device having flexible spaced portions proximal to the region of attachment such that when a distal force is applied to the pushing device the spaced portions bend outwardly from the pushing device thereby engaging the crown members of the crown to expand the crown.

In another embodiment the catheter comprises a balloon, and the stent is disposed about a portion of the balloon. The distal end of the pushing device includes a two member cantilever mechanism. A first member extends substantially parallel to a longitudinal axis of the catheter, and a second member extends proximally at an oblique angle from a region of attachment at the distal end of the first member. The first member and the second member are fixedly attached one to the other at a joining region. The joining region is fixedly engaged to the balloon with the distal end region of the pushing device extending between the first member and the second member. When the pushing device is advanced, the second member rotatingly engages the plurality of crown members to expand the crown.

Another embodiment is directed to a catheter wherein the pushing device includes a ring portion. The ring has a first portion and a second portion. The first portion being positioned proximal to the distal end region, and the second portion is positioned distal to the distal end region of pushing device. The ring portion rotatingly engages the plurality of crown members to expand the crown.

Another embodiment is directed to a catheter wherein the pushing device includes a plurality of web-like strands. The plurality of web-like strands is constructed and arranged to engage the plurality of crown members when the pushing device is advanced in a distal direction to a first predetermined distance. When the pushing device is advanced to a second predetermined distance, the plurality of web-like strands pulls the crown members to expand the crown.

BRIEF DESCRIPTION OF THE SEVERAL VIEWS OF THE DRAWINGS

A detailed description of the invention is hereafter described with specific reference being made to the following drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

As discussed above, the present invention is directed to a variety of bifurcated stents. The embodiments disclosed herein may be balloon expandable, self-expanding, or hybrid stents.

Figure 1:
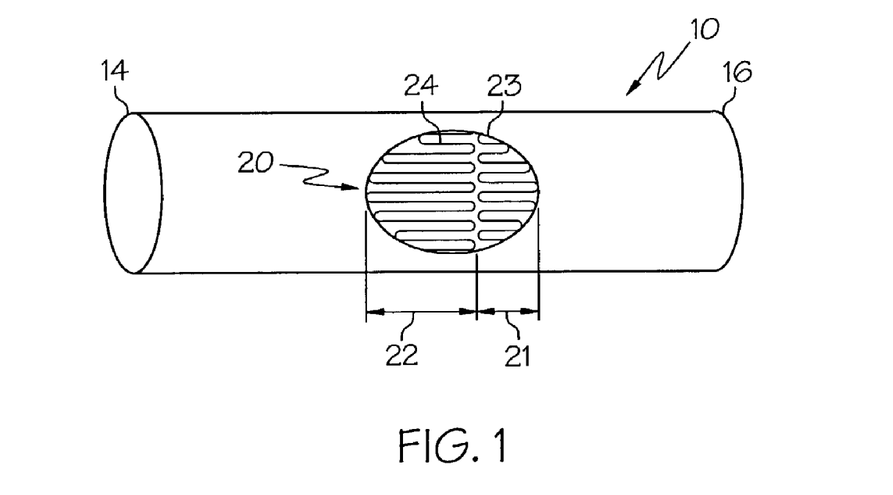
FIG. 1 is a side view of a stent with a crown.

A first embodiment of the invention is depicted in FIG. 1, wherein a stent, indicated generally at 10, is shown. The stent 10 can be self-expandable, balloon expandable or a hybrid and has a proximal end 14 and a distal end 16. Positioned between the distal and proximal ends of the stent 10 is a crown 20. The crown 20, having a distal portion 21 and a proximal portion 22, is defined by a cell opening 23 about which fingers 24 are positioned. The number of fingers 24 on the stent 10 can vary between 2 and 25. Upon expansion these fingers may extend into a bifurcation. As seen in FIG. 1, the fingers 24 may vary in length and the majority of the fingers 24 extend longitudinally in either a distal or proximal direction from the crown with some fingers 24 extending at an angle that is not longitudinal. However, for purposes of this embodiment, those fingers 24 that extend with a longitudinal component will be considered to be on a distal portion 21 of the crown 20 if a component of its extension from the crown 23 is in a proximal direction and will be considered on a proximal portion 22 of the crown 20 if a component of its extension from the crown 23 is in a distal direction. The distally extending fingers 24 are generally longer than the proximally extending fingers 24.

Figure 1A:
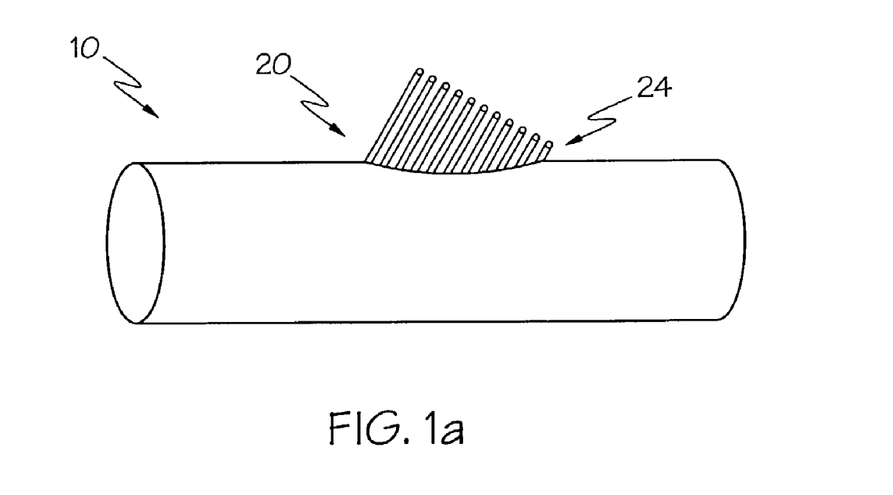
FIG. 1a is a side view of a stent with the crown expanded.

FIG. 1a illustrates an embodiment of the invention in which the fingers 24 positioned on crown 20 are in an expanded state. Among other things, the combination of longer and shorter fingers 24 is designed to provide better carina coverage. A desirable embodiment would have fingers 24 that decrease in length from the proximal to the distal end of the crown 20, and for that matter, from the distal to the proximal end of the crown 20. A more desirable embodiment would have a decrease of similar increments in the length of the fingers 24.

Figure 2:
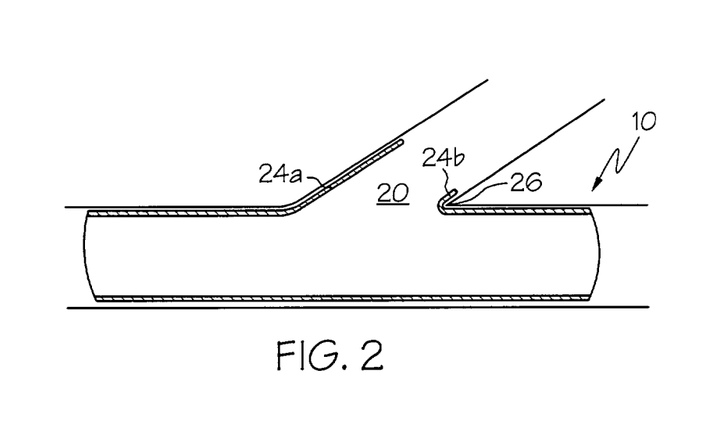
FIG. 2 is a cross-sectional view of an expanded stent with the asymmetrical crown fingers of the crown extended into a lumen.
Figure 2A:
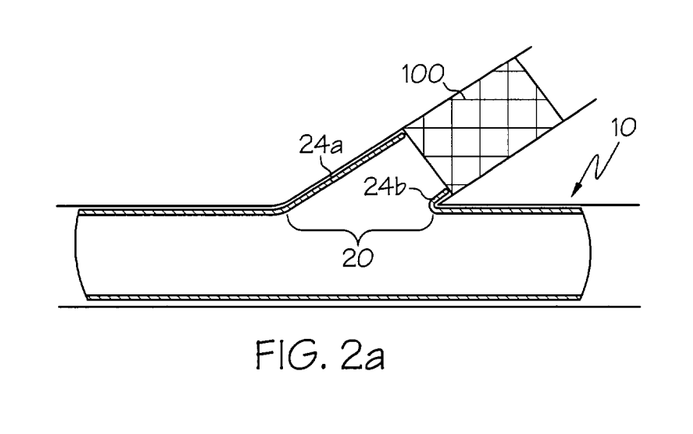
FIG. 2a is a cross-sectional view of an expanded stent with the asymmetrical fingers of the crown extended and engaging a stent in a secondary lumen.

FIG. 2 is a cross-sectional side view of an expanded stent 10 positioned at a bifurcation. The stent 10 includes crown 20 having longer fingers 24a and shorter fingers 24b which extend into the secondary lumen of the bifurcation. As illustrated in FIG. 2, shorter fingers 24b are located at the carina 26 of the bifurcation. The longer fingers 24a and shorter fingers 24b are designed to extend in such a way that support is provided at the bifurcation, and as illustrated in FIG. 2a, when attachment to another stent 100 in the secondary lumen is desired, there is no gap in coverage.

Figure 3:
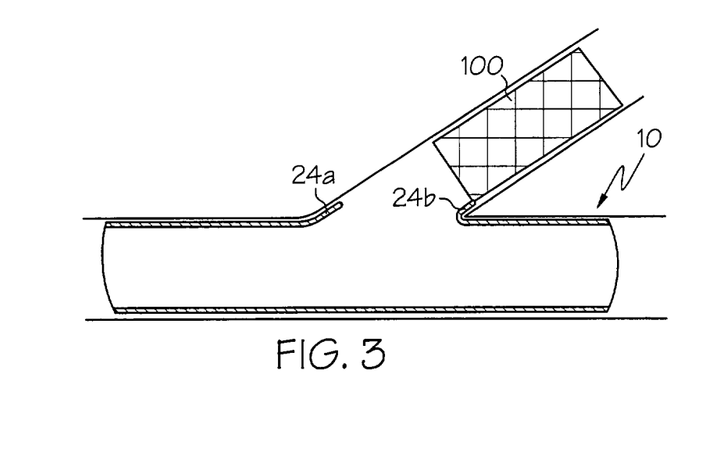
FIG. 3 is a cross-sectional view of an expanded stent with the equal-length fingers of the crown extended and engaging only a portion of the stent in the secondary lumen while leaving a gap on one side.
Figure 3A:
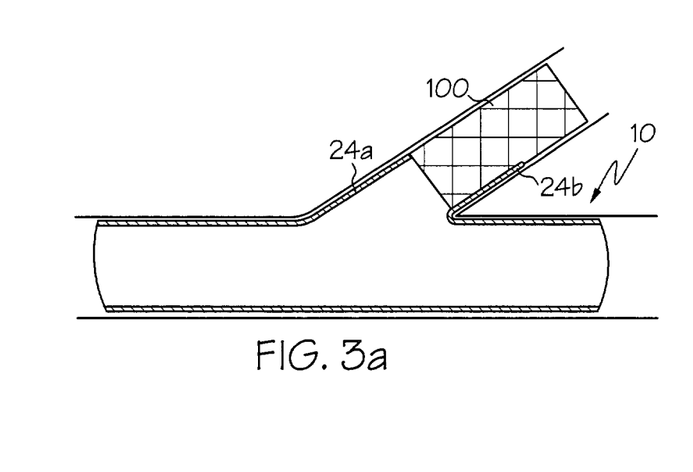
FIG. 3a is a cross-sectional view of an expanded stent with the equal-length fingers of the crown extended and engaging the stent in the secondary lumen while overlapping a portion of the stent in the secondary lumen.

FIGS. 3 and 3a illustrate two cases with lesser coverages. FIG. 3 depicts a bifurcation in which the fingers 24 of the stent 10 are of a short equal length. The stent 100 in the secondary lumen can only engage the fingers 24 at one location. Thus a portion of the secondary lumen at the bifurcation remains uncovered. FIG. 3a depicts a bifurcation in which the fingers 24 of the stent 10 are long but of equal length. In this example, the fingers 24 extend into the secondary lumen at the bifurcation. However, coverage is again not full because to obtain full coverage, it is necessary to overlap one portion of the fingers 24 with the stent 100 in the secondary lumen.

Figure 4A:
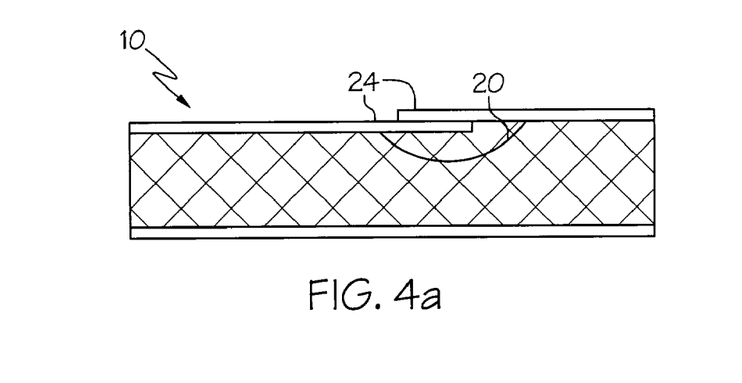
FIG. 4a is a cross-sectional view of a stent with a crown in which the fingers overlap.
Figure 4B:
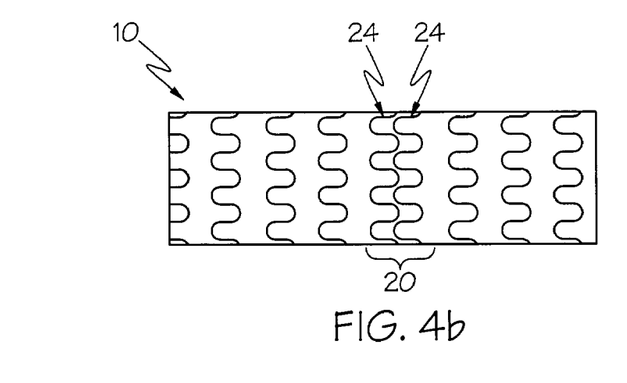
FIG. 4b is a cross-sectional view of a stent with a crown in which the fingers are interlaced.

FIG. 4a illustrates a stent 10 with a crown 20. The fingers 24 of the crown 20 overlap. In this embodiment the fingers 24 extending proximally overlap those extending distally. FIG. 4b illustrates a stent 10 with a crown 20. The fingers 24 of the crown 20 are interlaced.

Figure 5A:
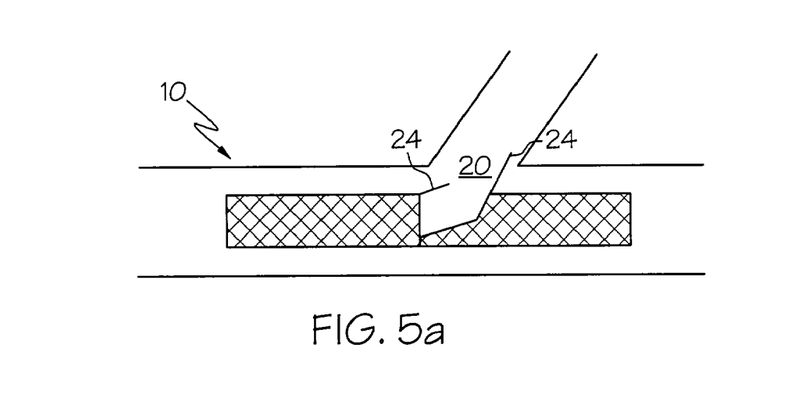
FIG. 5a is a cross-sectional view of a partially deployed stent with a crown in which the fingers are opening towards the secondary lumen.
Figure 5B:
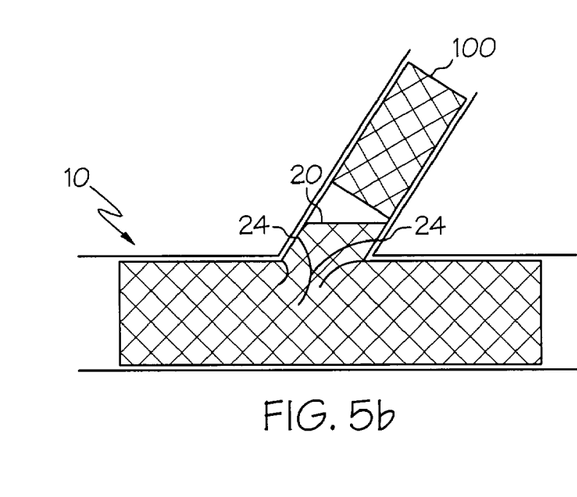
FIG. 5b is a cross-sectional view of a fully deployed stent with a crown in which the fingers extend into the secondary lumen to engage another stent.

FIG. 5a illustrates a stent 10, with a crown 20 that has longer fingers on the distal portion of the crown 20, inside a body lumen at the point of the bifurcation. In this embodiment the fingers 24 of the crown 20 begin to open before the main body of the stent 10 is fully deployed. Typically, treated bifurcations have a lumen opening 2.0 mm or greater. While the fingers can be of a length up to about 10.0 mm, for a finger 24 to flip into the bifurcated secondary lumen it is sometimes beneficial to limit the length of the finger 24 to about 1.5 mm to account for any misalignment in the placement of the stent 10. Because the fingers 24 must clear the walls of the carina of the secondary lumen, designing the crown 20 to begin opening before stent 10 is fully deployed allows the length of the fingers 24 to be longer than if the fingers 24 were extended into the secondary lumen after the full deployment of the stent 10. The fingers 24 can begin opening within the primary lumen before full deployment and thus have extra room in which to clear the apexes of the carina. FIG. 5b depicts the stent of FIG. 5a after full deployment. As shown, the distal portion of the carina has very good coverage. Here a second stent 100 is present in the secondary lumen.

Figure 6:
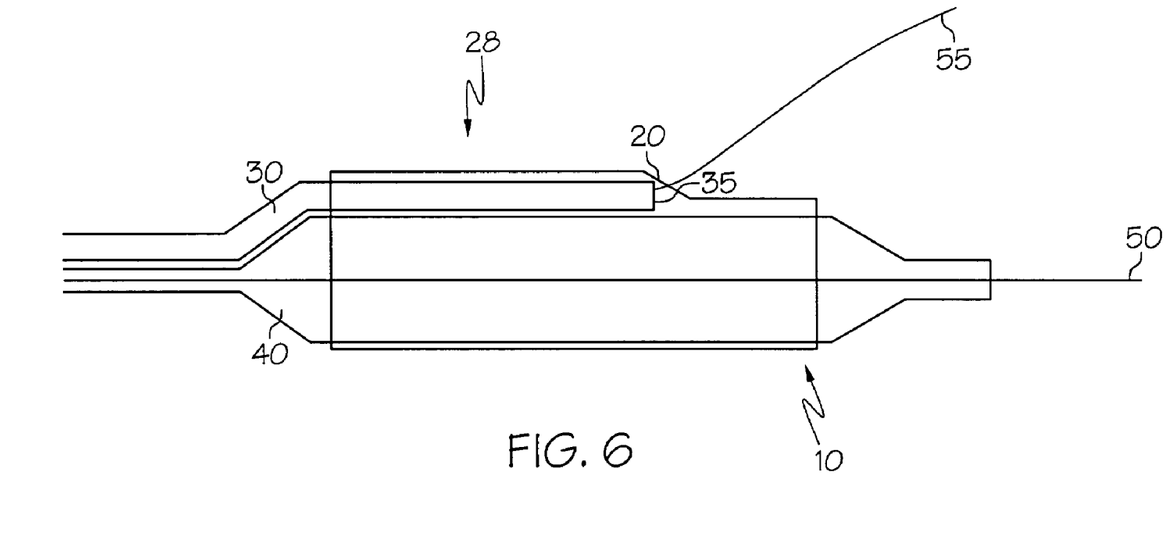
FIG. 6 is a side view of a stent with a crown and the stent deployment apparatus.

FIG. 6 illustrates an apparatus 28 for deploying a stent 10 with a crown 20 at a bifurcation. Though this can be done in a self expanding stent, a balloon 40 is shown with the apparatus 28. The stent 10 is guided along guidewire 50. A pushing device 30, with a push plate tip 35, is located alongside the catheter and balloon 40 and extends under the stent 10 to the crown portion 20 of the stent 10. The pushing device 30 is guided by a guidewire 55.

Figure 7:
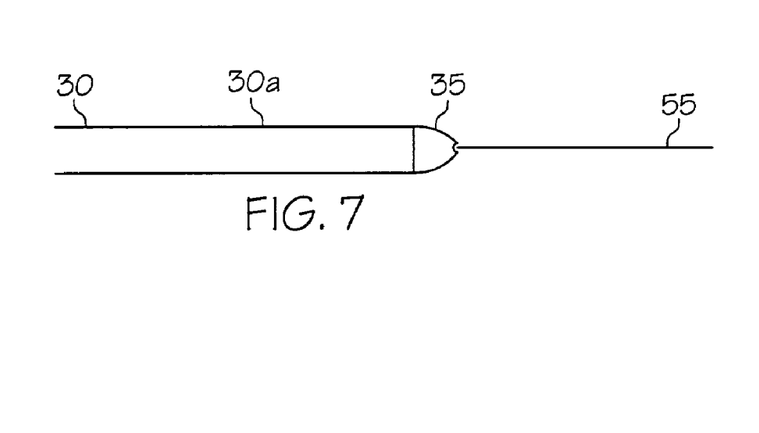
FIG. 7 is a perspective view of a possible push tip design.
Figure 7A:
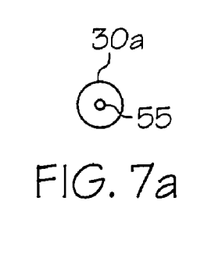
FIG. 7a is a view through a secondary lumen of the end view of the push tip.

In one embodiment of the pushing device, as shown in FIG. 7, pushing device 30 includes a push plate 30a with a tip 35. In this embodiment the push plate 30 is guided along guidewire 55 and pushed forward through the crown 20. The push plate 30a forces the fingers outwardly and into the secondary lumen. FIG. 7a illustrates the view through the secondary lumen after the push plate 30a has been pushed through.

Figure 8:
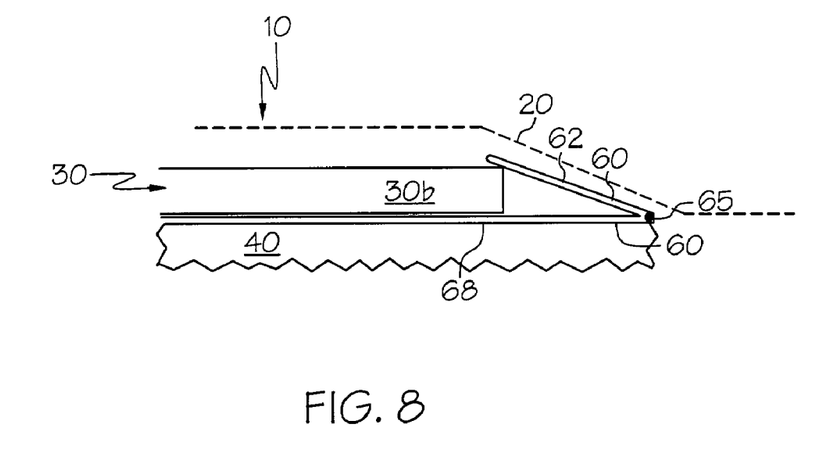
FIG. 8 is a cross-sectional view of a possible push plate design.
Figure 8A:
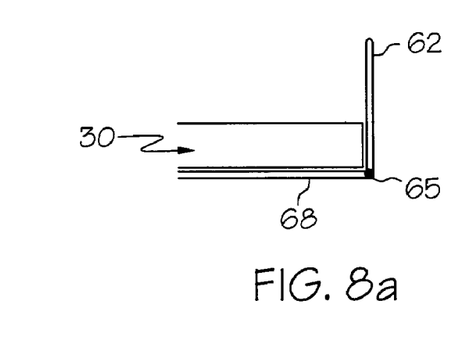
FIG. 8a is a cross-sectional view of the end view of the push plate.

FIG. 8 illustrates another embodiment. Here the pushing device 30 includes an engaging mechanism 60 which is moveably disposed between the balloon 40 and push plate 30b. The mechanism 60 includes a longitudinal member 68 which extends along at least a portion of balloon 40 and includes a cantilever member 62. Upon distal movement along the longitudinal member 68, the push plate 30b engages and rotates the cantilever member 62 about a pivot position 65. As the cantilever member 62 rotates, it engages the crown portion 20 of the stent 10 and opens the crown portion. FIG. 8a illustrates the end result of this movement.

Figure 9:
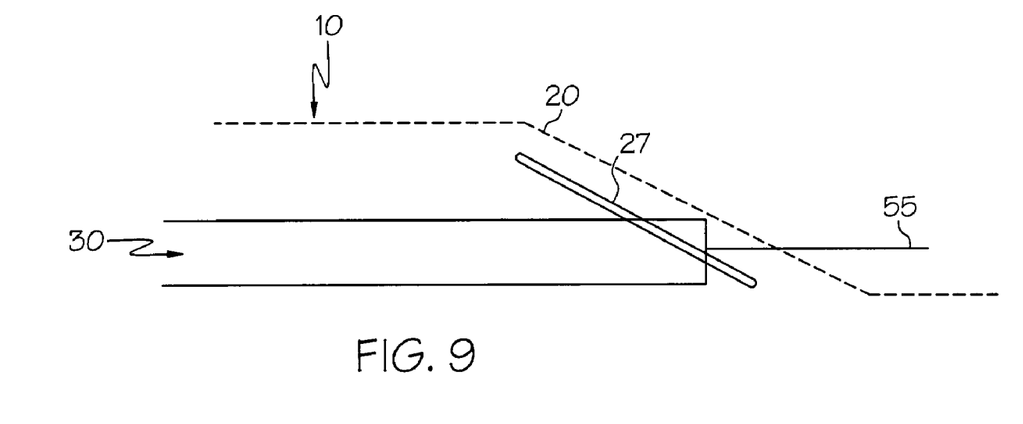
FIG. 9 is a cross-sectional view of a possible push plate design utilizing a ring.
Figure 9A:
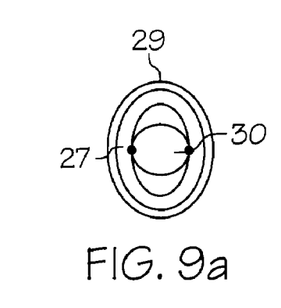
FIG. 9a is a view through a secondary lumen of the end view of the push plate.

FIG. 9 illustrates another embodiment in which a ring 27 is attached to the push device 30. The distal end of the ring 27 comes into contact with crown 20 and thereby rotates the proximal end of the ring so as to engage and force outward the fingers of the crown 20. In FIG. 9a a view through the secondary lumen is shown. The ring 27 has fully engaged the fingers and extended them into the lumen 29.

Figure 10:
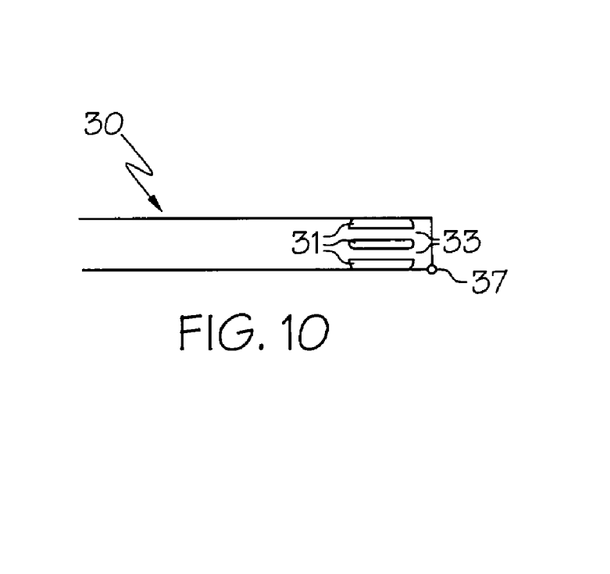
FIG. 10 is a perspective view of a possible push tip design having a fixed region and a distal end with spaced portions.
Figure 10A:
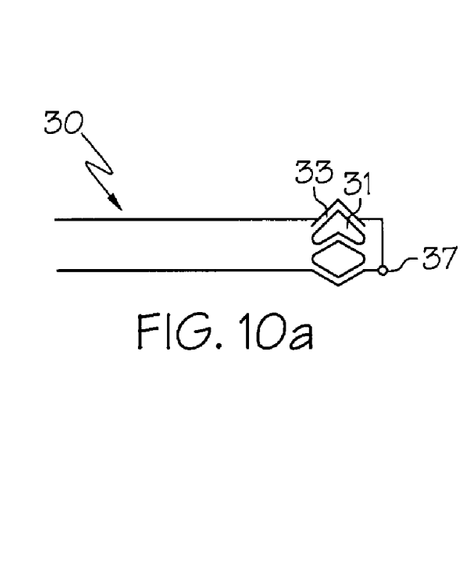
FIG. 10a is a perspective view of a possible push tip design in which distal force is applied and the distal spaced portions bend flaring outward.
Figure 10B:
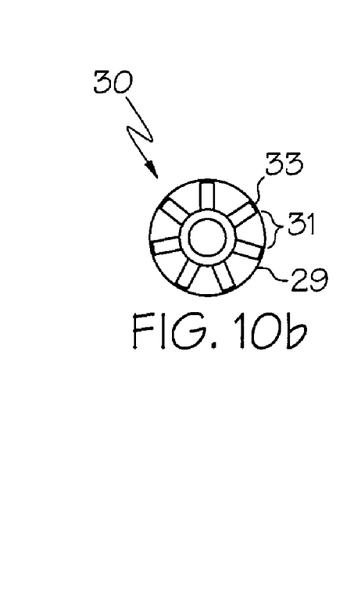
FIG. 10b is an end view through a secondary lumen of a possible push tip design in which the distal spaced portions are fully flared.

Another embodiment is illustrated in FIG. 10. Here the pushing device 30 is a tube or rod in which the distal end is hollow and has spaced openings 31 around the distal end. Between each of these openings 31 a strip 33 of flexible material is extant. As shown in FIG. 10a, when distal movement is applied to the pushing device 30, the strips 33 bend outward under a compressive force created due to the end of the tube or rod having a fixed region of attachment 37 fixedly attached to the balloon or to an embodiment of the longitudinal member 68 of FIG. 8. As the strips 33 flare outward, the fingers are contacted and forced outward into the secondary lumen 29. FIG. 10b illustrates the end result of this movement.

Figures 11, 11A, 11B:
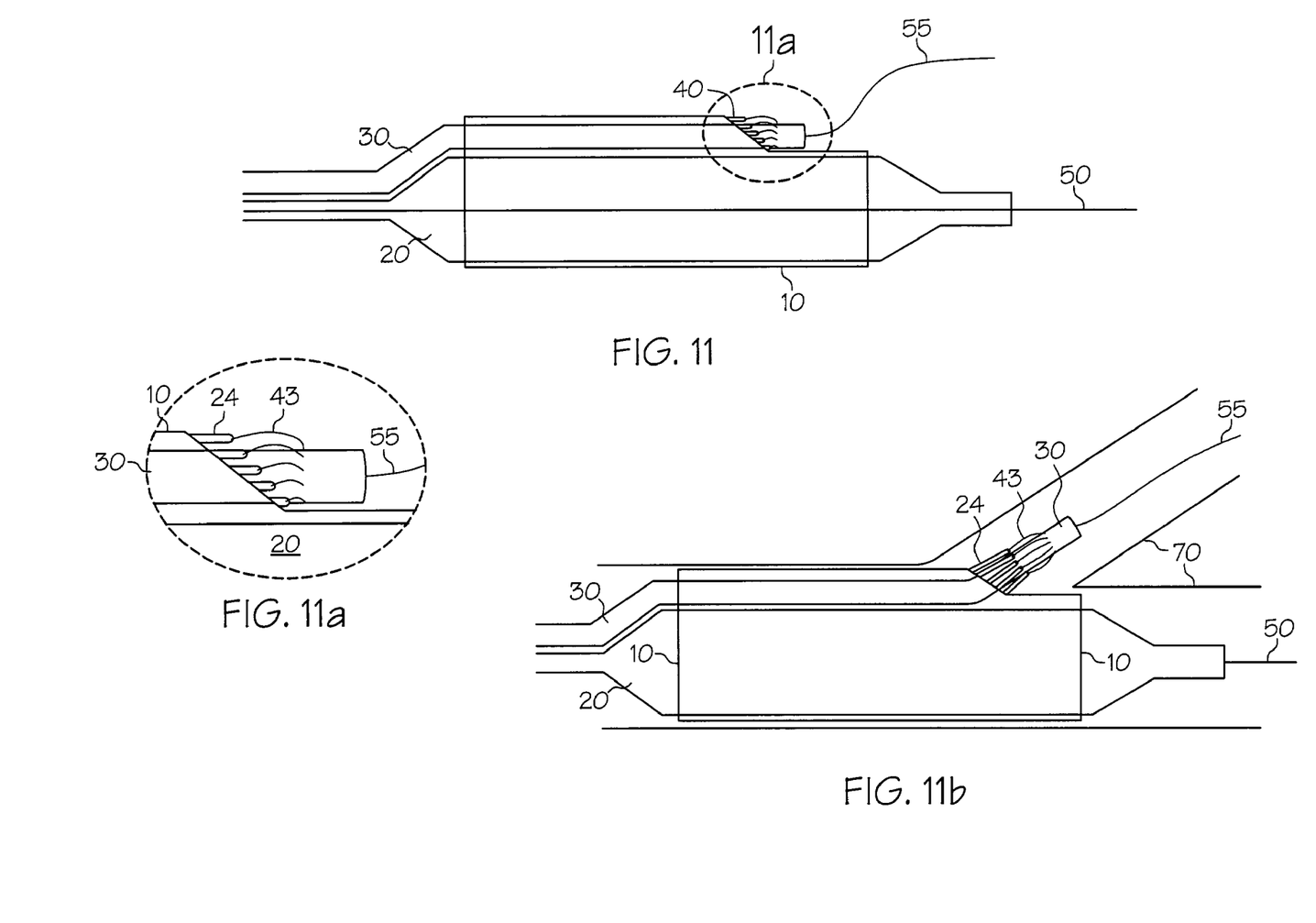
FIG. 11 is a side view of a stent with a crown and the stent deployment apparatus wherein the push tip is pulling the fingers outward.
FIG. 11a is a close-up view of the push tip with the pull wires engaging the crown fingers outward.
FIG. 11b is a side view of a stent with a crown and the stent deployment apparatus inside a body lumen wherein the push tip is pulling the fingers outward into a secondary lumen.

In FIGS. 11 and 11a another embodiment is illustrated. Here, a pushing device 30 includes web-like strands 43. When distal motion is applied to the device 30, the distal portion of device 30 will pass through the crown 40 and the strands 43 will engage the fingers 24 of the crown 40. In this manner a pulling motion is applied to the fingers 24 to deploy them. FIG. 11b illustrates a device that pulls the fingers 24 to deploy them within a body lumen 70. The web-like strands 43 break free from the fingers 24 when a certain distance is traveled. This can be done using a number of materials. One embodiment includes biophilial materials that break upon a designed-for tension. Another embodiment incorporates a material that acts in the manner of hook and loop material.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A stent comprising:
    a tubular structure having a first end and a second end, the tubular structure being disposed about a first longitudinal axis and having an expanded state and unexpanded state, a portion of the tubular structure defining a side opening, the side opening being substantially ring-shaped in the expanded state, the side opening having a perimeter and being located between the first end and the second end of the tubular structure, the perimeter having a first end and a second end;
    a first plurality of fingers extending from a first portion of the perimeter, each finger of the first plurality of fingers having a length, each finger of the first plurality of fingers extending from the tubular structure about a second longitudinal axis upon expansion of the stent, the second longitudinal axis being nonparallel to the first longitudinal axis, wherein successive fingers of the first plurality of fingers are of increasing length, the finger closest to the first end of the perimeter being shorter than the finger closest to the second end of the perimeter.

2. The stent of claim 1 having an outer surface defining a cylindrical plane wherein in an unexpanded state the fingers lie substantially within the cylindrical plane.

3. The stent of claim 1 wherein each of the fingers has a length less than 10.0 mm.

4. The stent of claim 1 wherein the stent is self-expanding.

5. The stent of claim 1 wherein the stent is balloon expandable.

6. The stent of claim 1 wherein all but at least one of the plurality of fingers are each adjacent to a finger having a smaller length and are adjacent to a finger having a longer length.

7. The stent of claim 1 wherein the plurality of fingers on the stent contains 2 to 25 fingers.

8. A stent comprising:
    a tubular structure having an expanded state and an unexpanded state and a proximal end and a distal end, the tubular structure being disposed about a first longitudinal axis and having an expanded state and unexpanded state, a portion of the tubular structure defining a side opening, the side opening being substantially ring-shaped in the expanded state, the side opening having a perimeter and being located between the proximal end and the distal end of the tubular structure;
    a first plurality of fingers and a second plurality of fingers,
        wherein in the unexpanded state, the first plurality of fingers extend distally in a substantially longitudinal direction from a first portion of the perimeter, each finger of the first plurality of fingers having a length, wherein successive fingers of the first plurality of fingers are of increasing length until a first maximum length is reached whereupon successive fingers of the first plurality are of decreasing length, and
        wherein in the unexpanded state, the second plurality of fingers extend proximally in a substantially longitudinal direction from a second portion of the perimeter, each finger of the second plurality of fingers having a length, wherein successive fingers of the second plurality of fingers are of increasing length until a second maximum length is reached whereupon successive fingers of the second plurality are of decreasing length, the first maximum length being greater than second maximum length, and
        wherein in the expanded state, each finger of the first plurality of fingers and the second plurality of fingers extends from the tubular structure about a second longitudinal axis, the second longitudinal axis being nonparallel to the first longitudinal axis.

9. The stent of claim 8, wherein each finger of the first plurality of fingers and the second plurality of fingers has a peak, and wherein in the unexpanded state the peaks of the first plurality of fingers are substantially aligned with each other about the circumference of the stent and the peaks of the second plurality of fingers are substantially aligned with each other about the circumference of the stent.

* * * * *